(12) United States Patent
Seyler et al.

(10) Patent No.: US 9,554,949 B2
(45) Date of Patent: Jan. 31, 2017

(54) APERTURED FORMED FILM WITH A PATTERN OF APERTURES AND A PLURALITY OF LIGHT TRAP MICRO-PITS

(71) Applicant: Tredegar Film Products Corporation, Richmond, VA (US)

(72) Inventors: Rickey J. Seyler, Chesterfield, VA (US); Paul Eugene Thomas, Terre Haute, IN (US); Andrew D. Maschino, Terre Haute, IL (US)

(73) Assignee: TREDEGAR FILM PRODUCTS CORPORATION, Richmond, VA (US)

( * ) Notice: Subject to any disclaimer, the term of this patent is extended or adjusted under 35 U.S.C. 154(b) by 371 days.

(21) Appl. No.: 14/023,017

(22) Filed: Sep. 10, 2013

(65) Prior Publication Data

US 2014/0087130 A1    Mar. 27, 2014

Related U.S. Application Data

(60) Provisional application No. 61/699,201, filed on Sep. 10, 2012.

(51) Int. Cl.
| | | |
|---|---|---|
| *B32B 3/24* | (2006.01) | |
| *A61F 13/512* | (2006.01) | |
| *A61F 13/511* | (2006.01) | |
| *A61F 13/513* | (2006.01) | |
| *B29C 43/22* | (2006.01) | |
| *B26F 1/26* | (2006.01) | |
| *B29C 59/06* | (2006.01) | |
| *B26D 7/01* | (2006.01) | |

(52) U.S. Cl.
CPC ....... *A61F 13/5126* (2013.01); *A61F 13/5121* (2013.01); *A61F 13/5125* (2013.01); *A61F 13/51104* (2013.01); *A61F 13/51394* (2013.01); *B26F 1/26* (2013.01); *B29C 43/222* (2013.01); *A61F 2013/51338* (2013.01); *B26D 7/018* (2013.01); *B29C 59/06* (2013.01); *Y10T 428/24273* (2015.01)

(58) Field of Classification Search
CPC .................. Y10T 428/24273; A61F 13/5125; A61F 13/51394
See application file for complete search history.

(56) References Cited

U.S. PATENT DOCUMENTS 4,463,045 A  *  7/1984  Ahr ................... A61F 13/15731
                                          428/131
2010/0230857 A1     9/2010  Muhs et al.

FOREIGN PATENT DOCUMENTS

| EP | 0 156 471 A2 | 10/1985 |
| EP | 2 184 041 A2 | 5/2010 |
| WO | WO 2011/112213 A1 | 9/2011 |

* cited by examiner

*Primary Examiner* — William P Watkins, III
(74) *Attorney, Agent, or Firm* — Thomas & Karceski, PC

(57) ABSTRACT

An apertured film with a reduced gloss through the use of light trap micro-pits uniformly distributed on the lands of the film in a random pattern and a method of making the same.

8 Claims, 14 Drawing Sheets

APERTURED FORMED FILM WITH A PATTERN OF APERTURES AND A PLURALITY OF LIGHT TRAP MICRO-PITS

CROSS-REFERENCE TO RELATED APPLICATIONS

This application claims the benefit of U.S. Provisional Application No. 61/699,201, filed Sep. 10, 2012, the disclosures of which are incorporated herein by references in their entirety.

FIELD OF THE INVENTION

The present application relates to polymeric films having a particular structure including a plurality of light trap micro-pits and apertures to give a reduced 75° gloss in the machine direction.

BACKGROUND OF THE INVENTION

It is extremely desirable to construct disposable articles, such as absorptive devices, including sanitary napkins, panty liners, interlabial devices, diapers, training pants, incontinent devices, wound dressings and the like to have a cloth-like feel and a reduction in gloss for a plastic film topsheet. An absorptive device is typically comprised of a topsheet against the user's skin, the option of an acquisition distribution layer disposed beneath the topsheet, an absorbent core affixed between the topsheet and a barrier layer and a barrier layer that is also called a backsheet. Absorptive devices are more desirable when enhanced with a soft cloth-like surface feel to the user's skin at any anticipated points of contact. Likewise, by having a topsheet that is a soft, cloth-like body-facing surface that retains a dry surface feel during use, an absorptive device gives improved wearing comfort, and minimizes the development of undesirable skin conditions due to prolonged exposure to moisture absorbed within the absorptive device.

Topsheets comprised of macroscopically expanded, three dimensional, apertured polymeric webs have been shown to exhibit desirable fluid transport and fluid retaining characteristics. Desirable fluid transport characteristics allow the topsheet to acquire fluids, such as urine or menses, and pass the fluid into the absorptive article. Once absorbed into the absorptive article, the fluid retaining feature of the topsheet preferably prevents rewet, i.e., the movement of fluid back through the topsheet.

U.S. Pat. No. 4,463,045 (Ahr et al.) discusses an apertured macroscopically expanded three-dimensional polymeric web that exhibits a substantially non-glossy visible surface and cloth-like tactile impression. Ahr et al. teaches the criteria which must be met with respect to the regularly spaced pattern of surface aberrations in order to diffusely reflect incident light and thereby reduce the gloss. Despite its advancements in eliminating gloss, the structure of the surface aberrations of the web in Ahr, et al. can lack desired softness and pose manufacturing difficulties in reliably making the regularly spaced pattern of surface aberrations.

U.S. Pat. No. 4,327,730 (Sorensen) discusses a multiplicity of "nubbles" to provides a cloth-like feel and a reduction in gloss for a plastic film topsheet. The nubbles are discusses as being spherical or spheroidal in cross-section having a cross-sectional diameter of from about 0.0005 inches to about 0.0110 inches (0.0127 mm to about 0.279 mm).

However, improvements in the reduction of gloss from polymeric webs used as topsheets while maintaining desired softness still remain an existing need.

SUMMARY OF THE INVENTION

An apertured film comprising an apertured film surface area comprising a pattern of apertures and lands surrounding the apertures, the lands comprising a land area; the land area comprising a uniform, random pattern of light trap micro-pits and a total reflective area, the light trap micro-pits comprising an opening, a sidewall descending from the opening to a bottom; the opening of the light trap micro-pit comprises an average diameter and a depth greater than the average diameter of the micro-pit divided by tan 75°.

A method for forming an apertured film with light trap micro-pits the method comprising: receiving a molten polymer web at an impingement point between a screen and a roller comprising a roller surface structure for forming the light trap micro-pits; forming the light trap micro-pits in the molten polymer web by contacting the molten polymer web to the roller surface structure forming a polymer web with light trap micro-pits; passing the polymer web with light trap micro-pits over a zone of a pressure differential such that the polymer web with light trap micro-pits extends through the screen forming the apertured film with light trap micro-pits.

DETAILED DESCRIPTION OF THE INVENTION

Figure 1:
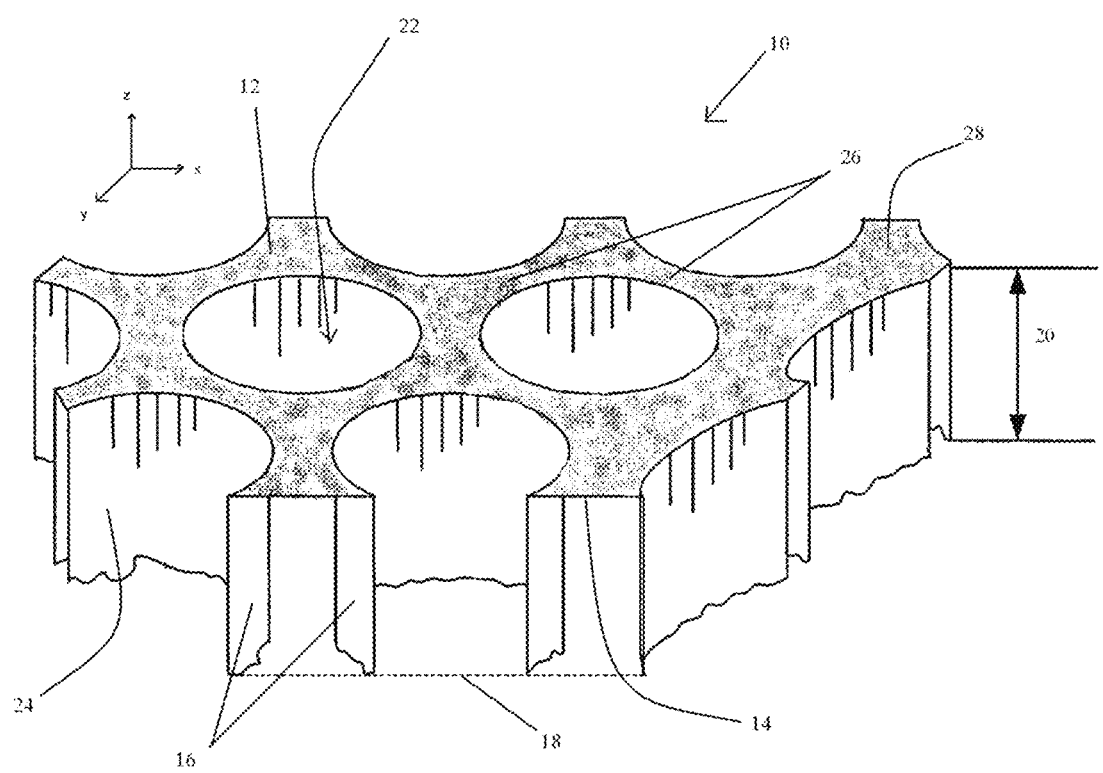
FIG. 1 is a perspective magnified view of portion of an apertured film with light trap micro-pits
Figure 2:
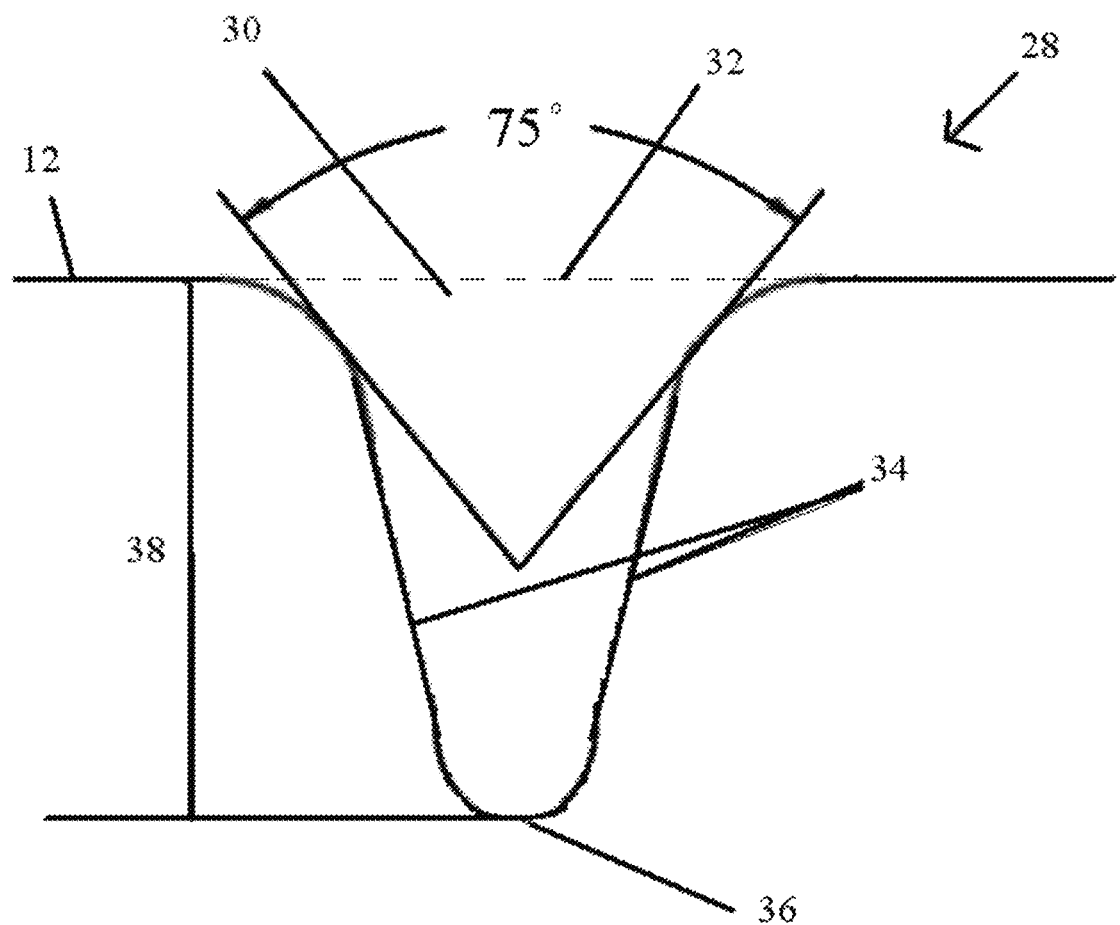
FIG. 2 is a cross-sectional magnified view of a representation of a light trap micro-pit with an included angle of 75°.

Apertured formed films used in disposable articles as topsheets are best received by consumers if gloss is absent.

A 75° Gloss measured in the Machine Direction (MD—i.e., the length of the film) is typically used to determine this attribute. While a 75° gloss of the film in the machine direction of less than 6.5 is acceptable, a gloss of about 3.5 or less is preferred, such as about 1 to about 3.5. The 75° gloss of the film may be on either side of the film, but the general plane used for the body facing side of an absorptive device comprises the reduced gloss. The film may comprise a plastic or polymer, such as a thermoplastic polyolefin. The polyolefin may comprise at least one of polyethylene, polypropylene, low density polyethylene, or high density polyethylene.

U.S. Pat. No. 4,463,045 discusses the substantial elimination of specular reflection in an a macroscopically expanded three-dimensional plastic web via regularly spaced, microscopic patterns of surface aberrations of protuberances projecting generally outwardly from the surface of the web or depressions projecting generally inwardly from the surface of the web.

The general plane of the film correlates to the primary plane of a forming screen surface used to make the film. Regular microscopic patterns prove to be difficult to replicate on commercial scale reliably. Additionally the diffuse reflectance is believed to be improved with a non-regular pattern such as the one described below.

The apertured film with light trap micro-pits 10 comprises a three-dimensional structure comprising a machine direction (MD) (y-dimension), a cross-direction (CD) perpendicular to the machine direction (x-dimension) and a z-direction. The z-direction comprises a first side 12, a film thickness 14, a second side 16 and a male surface 18. The distance from the first side 12 to the male surface 18 is the loft 20 of the film 10. Before being apertured, a precursor material comprises a first side, a material thickness and a second side; wherein the first side and second side are separated in the z-direction by the material thickness. The precursor material may be a molten polymer web or it may be a film. The precursor material is then modified to create a three-dimensional structure, such as by aperturing the precursor material, to create the male surface 18, which extends in the z-direction away from the second side 16 of the apertured film 10. The apertured film 10 comprises a series of apertures 24, each aperture 24 comprising an aperture sidewall 24 which extends from the first surface 12 to the male surface 18. The series of apertures 24 are encompassed in the first surface 12 by lands 26. The lands 26 further comprise a plurality of light trap micro-pits 28. The first surface 12 of the apertured film is also referred to herein as a general plane.

The film of the present application comprises a plurality of light trap micro-pits 28. As used herein a "light trap micro-pit" means a micro-pit or a negative depression in the first surface 12 of the apertured film 10, the micro-pit 26 comprising a micro-pit opening 30 having a micro-pit opening diameter 32, a micro-pit sidewall 34 descending from the micro-pit opening 30 to a micro-pit bottom 36. An example of a light trap micro-pit 28 from a cross sectional view can be seen in FIG. 1. The micro-pit opening 30 of the light trap micro-pit 28 may have a generally circular shaped diameter 32 when viewed from the general plane of the film 10, however, the diameter 32 may be variable in shape and thus comprises an average diameter derived from taking several measurements across its generally irregular perimeter and a depth 38 (from the micro-pit opening 32 to the micro-pit bottom 36) such that an included angle of 75° cannot reach the bottom 36 of the light trap micro-pit 28. The micro-pit sidewalls 34 descend with irregularity from the general plane 12; that is to say, the micro-pit sidewalls 34 are not comprised of generally straight or linear shape. The bottom 36 is located in the thickness 14 of the film 10 between the general plane 12 and the second side 16. In other words, the micro-pit sidewall 34 of does not extend through the thickness 14 of the film 10 to create holes in the film 10.

The light trap micro-pit average diameter is no more than about 250 µm and no less than about 25 µm. Larger micro-pit average diameters will not fit on a land 26 of the film 10 at the preferred spacing when the lands 26 are constructed such that the total reflective area of the lands 26 is satisfactory. Additionally, it is believed that smaller average diameter would not achieve a depth which will functionally trap light from reflection out of the micro-pit 28.

The light trap micro-pit depth 38 must meet the requirement of being such that the included 75° angle cannot reach the light trap micro-pit bottom 36 thus the required depth 38 is mathematical derivation dependent on the average diameter of the light trap micro-pit. For example, the depth 38 of the micro-pit is greater than half the average diameter of the micro-pit divided by tan θ (here θ is 37.5°). Assuming the rays adjacent to the 75° angle are of equal length, bifurcating the angle in half (37.5°) and bifurcating the average diameter of the micro pit in half, trigonometry defines the half of the average diameter as the opposite leg of the 37.5° angle and the bifurcating ray as the adjacent leg of the 37.5° angle. Without being limited by a theory, it is believe that light is 'trapped' in such a micro-pit 28 structure and the light cannot fully be reflected back out the micro-pit 28 structure resulting in a gloss reduction on the general plane 12 of the film 10. The gloss may be measured in the machine direction of the film 10 such that the 75° gloss is less than about 4.0, preferably less than about 3.5.

Micro-pits 28 of various light trap dimensions can be randomly positioned on the land area 26 provided the micro-pits 28 are not spaced apart too widely such that the non-pitted surface between the light trap micro-pits 28 reflects the light and nullifies their light trap effect of lower gloss. The random positions are uniform in density across the land area 26 rather than only concentrated in particular locations in the land area 26.

Figure 3:
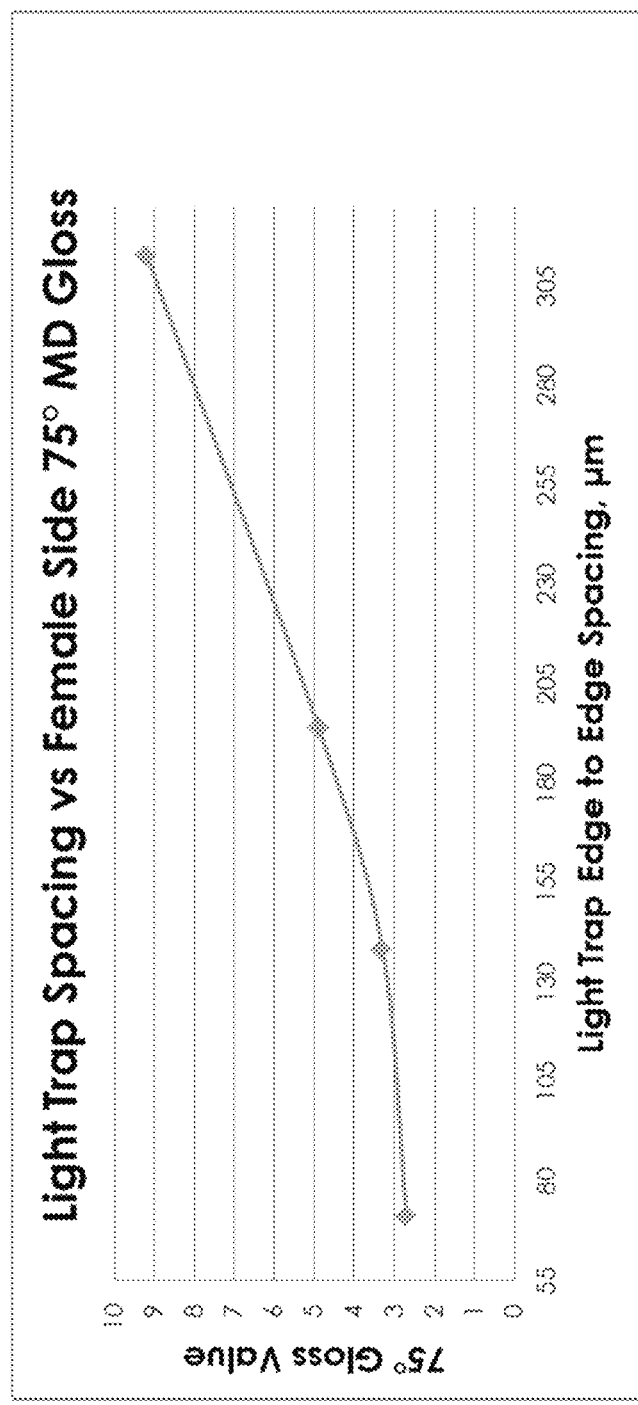
FIG. 3 is a graphical representation of the desired edge-to-edge spacing of the diameters of light trap micro-pits for reducing of 75° gloss in the machine direction of a film described herein.

The graph of FIG. 3 shows that if the spacing of the light trap micro-pit have an edge-to-edge spacing of greater than about 155 µm exists between the edges of two different light trap micro-pit perimeters, there exits enough non-micro-pitted film surface (total reflective area) in the general plane to raise the gloss value. Without being limited by a theory, non-micro-pitted existing between spacing at about 155 µm or less between edges of two different light trap micro-pit perimeters will not reflect enough light to nullify the gloss reduction of the light trap micro-pits and a 75° gloss of less than about 3.5 of the film surface (general plane) 12 in the machine direction is attainable.

Figure 4:
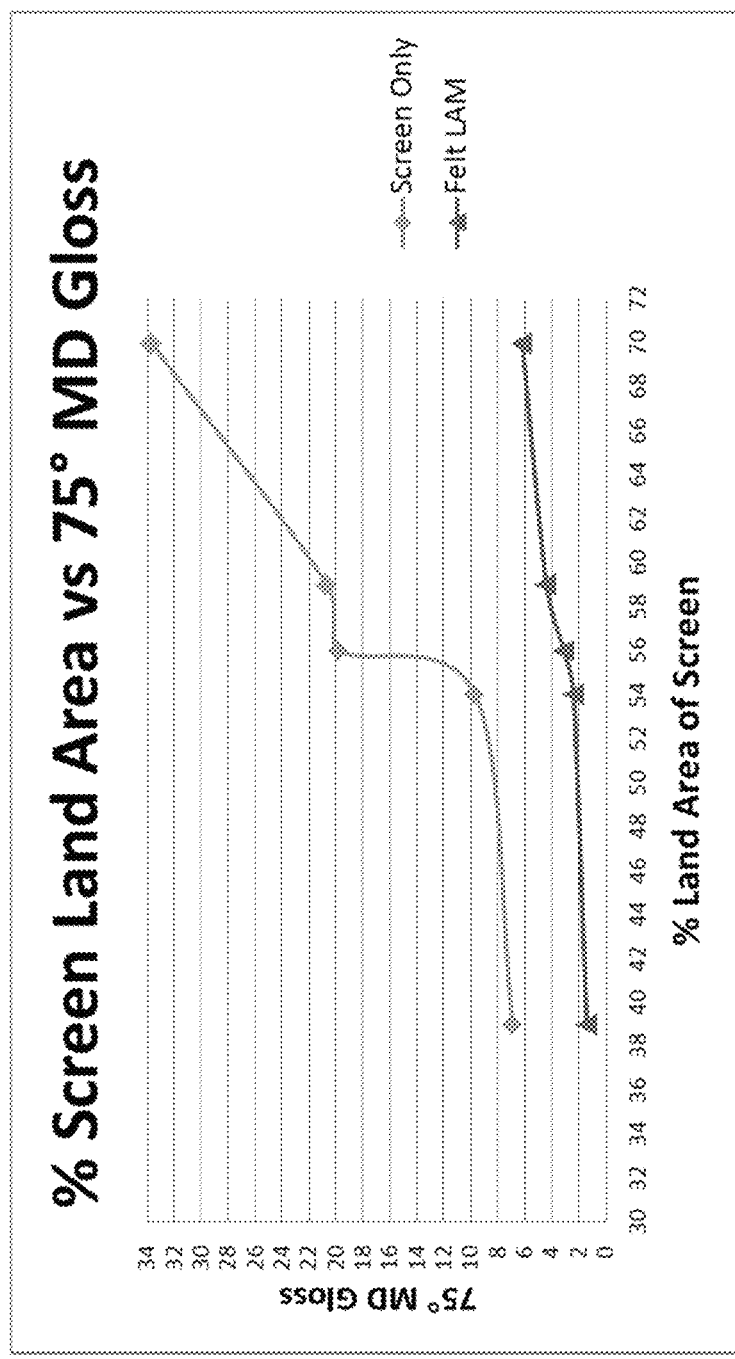
FIG. 4 is a graphical representation of the desired land area of the forming screen for reducing of 75° gloss in the machine direction of a film described herein.
Figure 5:
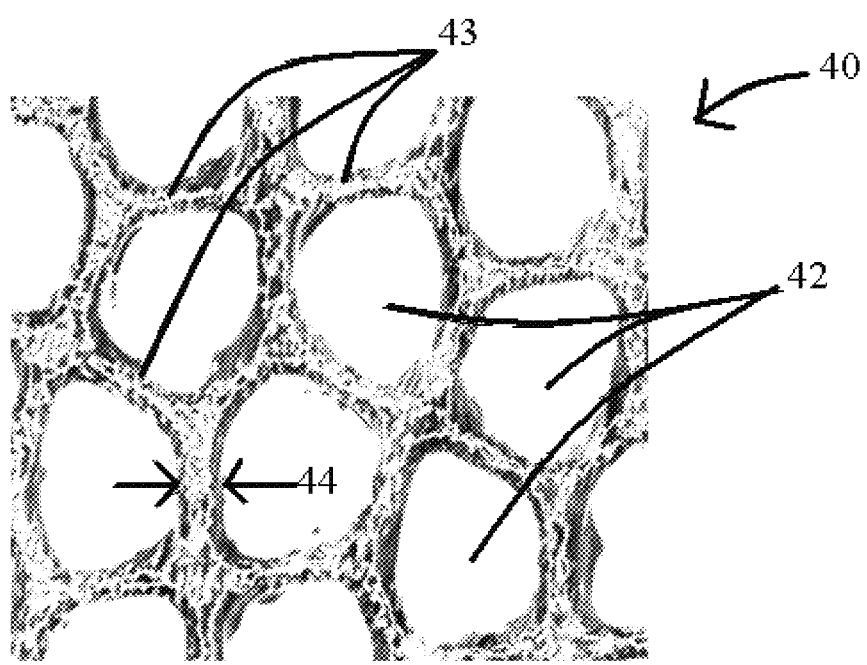
FIG. 5 is a micro-graph picture of a 50/7 pattern in the film.
Figure 6:
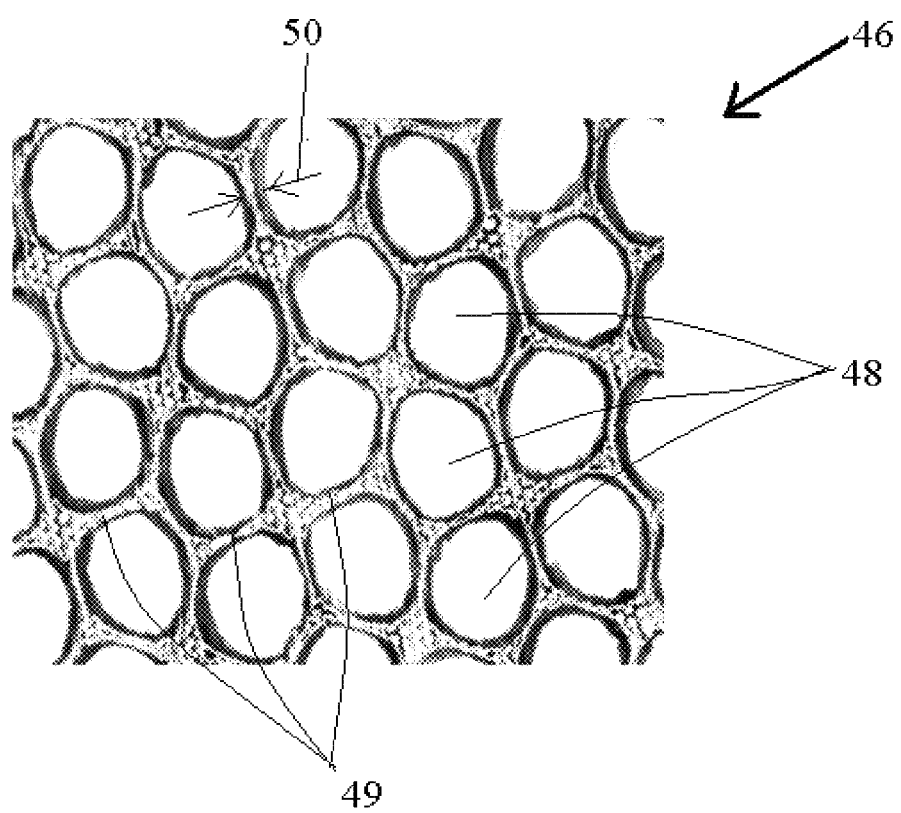
FIG. 6 is a micro-graph picture of a comparative example 35/7 pattern in the film.

The general plane 12 of an apertured film 10 comprises one or more apertures 22 and lands 26. These lands 26 are the structures surrounding the aperture 22 in the general plane 12. The apertures 22 are negative spaces which pass from the general plane 12 of the film through the film thickness 14 and terminate on the male surface 18 of the film giving a three-dimensional structure in the z-direction. The surface areas of the land structures 26 in the general plane 12 combine for the "land area". Any type of pattern for apertures 22 in the apertured films 10 may be utilized and is not limited to the embodiment discussed specifically herein. FIGS. 4-6 are micro-images looking down onto the general plane 12 of the lands 26 and the aperture 22 patterns. FIG. 4 shows a 50/7 film pattern 40 comprising an aperture 42 with a diameter of 50 mils (1270 microns), a land 43 and an average land width 44 of about 7 mils (178 microns). FIG. 5 shows an example with a 35/7 pattern 46 comprising an aperture 48 with a diameter of 35 mils (889 microns) diameter, a land 49 and an average land width 50 of about 7 mils (177.8 microns). FIG. 6 shows an example with a 35/14 pattern 52 comprising an aperture diameter 54 of 35 mils (889 microns), a land 55 and an average land width 56 of about 14 mils (355.6 microns). In one embodiment, the apertured film 10 comprises a pattern of apertures 22 whose perimeter geometry is substantially a pentagon with a flat to tip opening dimension of 1270 microns, arranged in a pattern of nested pentagons with a substantially uniform land 26 between the apertures 22 defining a land width of about 178 microns yielding a land area of about 40% of the total surface area.

The graph of FIG. 4 shows that a total land area of less than about 60% of the total surface area when combined with light trap micropits reduces the 75° gloss of the film surface (general plane) in the machine direction below 4.0.

In one embodiment the surface areas of the land structures further comprise a light diffracting pattern, such as a series of random humps and valleys that extend away from the general plane of the film. The light diffracting pattern may be in a defined pattern or a random pattern, either of which is of a greater magnitude and scale than the scale of the light trap micro-pits described above for the film. The light diffracting pattern may result from the way the film is manufactured, such as physical shape of the forming screen used to make the film structure. The general plane of the film correlates to the primary plane of a forming screen surface used to make the film. The light diffracting pattern would correspond to structures extended from the primary plane of the forming screen.

Forming Screen

The forming screen 58 comprises a primary plane 60 and a secondary plane 62 with screen thickness 64 between the primary plane 60 and the secondary plane 62. The physical shape of the screen determines the geometric pattern of apertures 22 on the film 10 and thus contributes to its aesthetic, tactile and mechanical properties. The primary plane 60 of the forming screen may comprise a smooth surface or it may comprise a light diffracting pattern, such as a series of random humps and valleys that extend away from the primary plane in the z-direction. The light diffracting pattern may be in a random pattern or a defined pattern that is of a greater magnitude and scale than the scale of the light trap micro-pits described above for the film. The light diffracting pattern of metal forming screens 58 may result from methods such as sand blasting the primary surface of the forming screen 58 with large grit particles; plasma coating the primary surface of the forming screen 58 with molybdenum or other suitable metal; flame spraying the primary surface of the forming screen 58 with brass, copper, or other metals; using an adhesive coating with particles (see Sorensen U.S. Pat. No. 4,327,730) on the primary plane 60 of the forming screen 58. If a rubber or polymer forming screen is used, a rough finish grind or laser disruption and other means can be applied to cause the humps and valleys that enhance the reduction of gloss.

Figure 7:
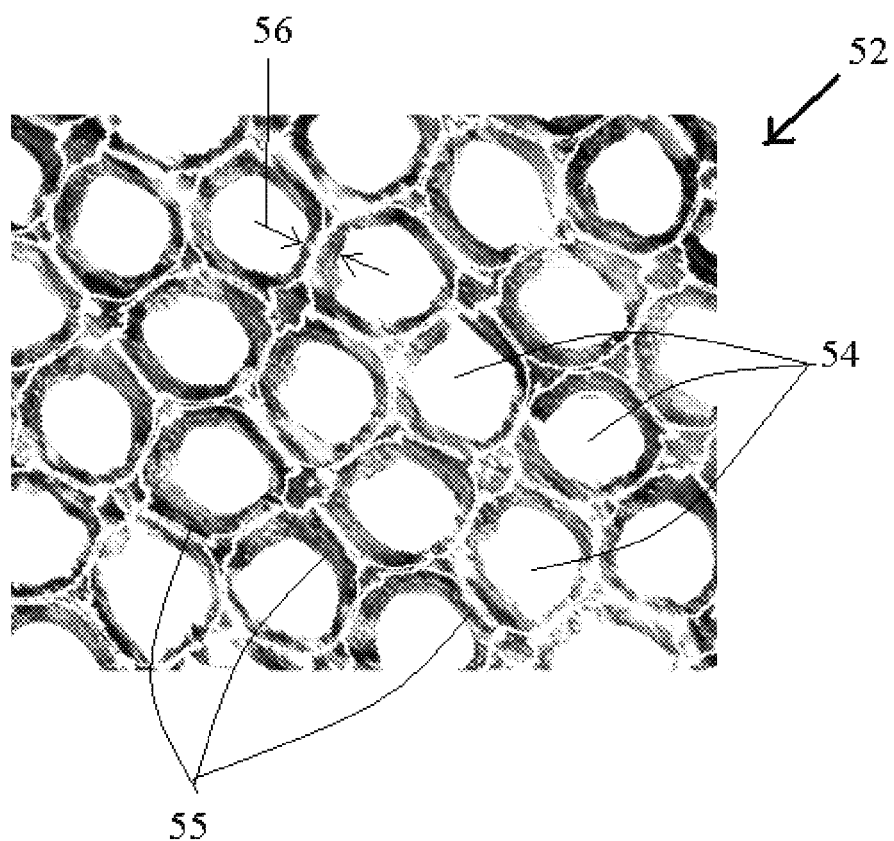
FIG. 7 is a micro-graph picture of a comparative example 35/14 pattern in the film.
Figure 8:
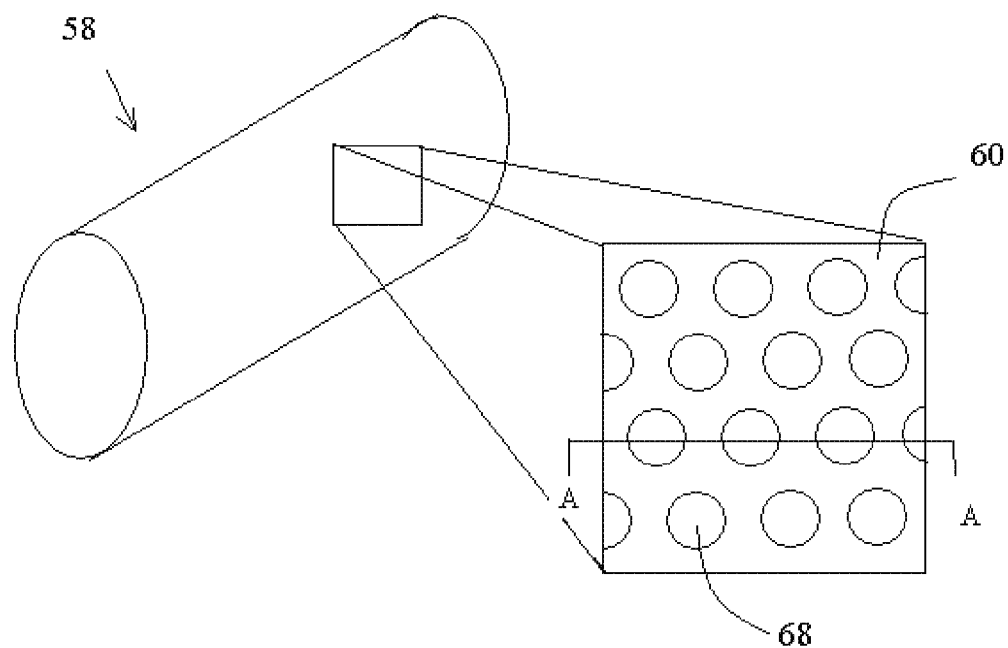
FIG. 8 is a front view of the screen with a magnified portion of the screen.
Figure 9:
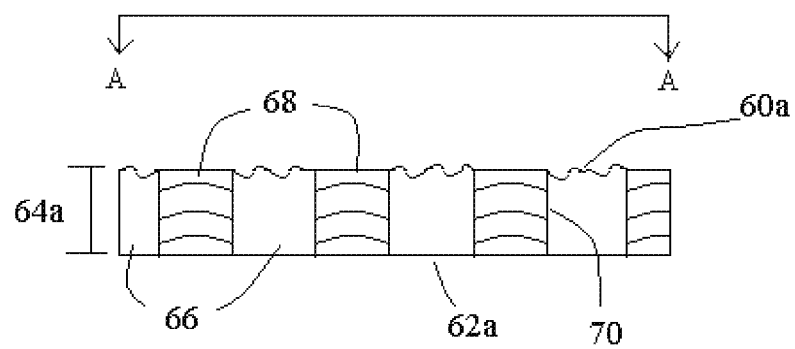
FIG. 9 is a cross-sectional view of an embodiment of the screen across A-A of FIG. 8.

FIGS. 8 and 9 show cross-sections of two different embodiments for the forming screen 58 taken generally along a similar line such as line A-A of FIG. 7. FIGS. 8 and 9 have a primary plane 60 (metal land outer surface) that is connected to the secondary plane (metal land inner surface) 62 by the screen thickness 64. The forming screen 58 comprises screen lands 66 and screen apertures 68, the screen apertures 68 extending from the primary plane 60 to the secondary plane 62 by screen aperture sidewalls 70. The screen lands 66 exist between screen apertures 68. Both secondary plane (inner land surface) 62a and 62b are smooth in texture as they must traverse smoothly over a vacuum slot seal during the formation of the apertures in the film from the precursor material. However, unlike primary plane (outer land surface) 60b, which is also smooth, in the preferred embodiment, primary plane (outer land surface) 60a, comprises humps and valleys such as those described above as light diffracting pattern.

The primary structures of the apertured formed film 10 is essentially a replicate of the forming screen's 58 structure. The forming screen 56 is useful as part of the method of making the film 10 described herein.

The apertured formed film comprises a thermoplastic polymer which may be formed into flexible film or sheets. Exemplary thermoplastic materials include polyolefins such as polyethylene and polypropylene, polyesters, polyvinyl alcohol, polystyrenes, polyamines, vinyl polymersmethyl methacrylates cellulose esters, and mixed thereof and other thermoplastic polymers which may be formed into flexible film or sheet, and the like. The polymeric film may be a low density polyethylene. Polymeric film may also comprise materials such as plasticizers and other additives known in the art may be added to achieve the desired physical characteristics for the polymeric film.

Absorptive Device

Figure 10:
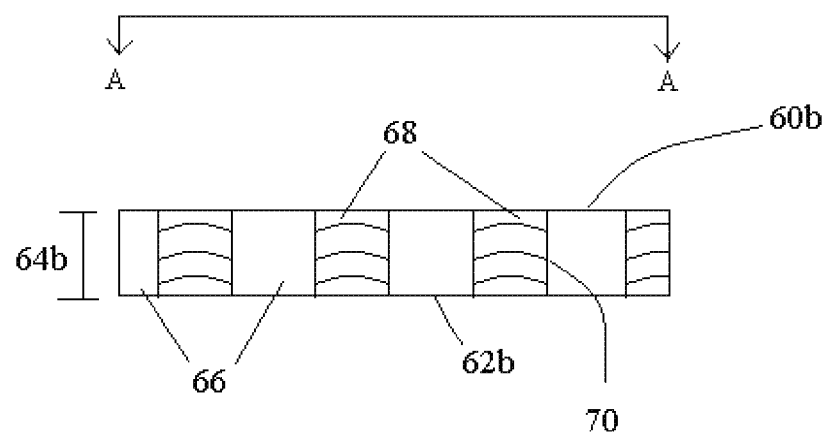
FIG. 10 is a cross-sectional view of an embodiment of the screen across A-A of FIG. 8.

As used herein, "absorbent article" includes diapers, incontinent articles, sanitary napkins, pantiliners, bandages, and other articles used to absorb body exudates. FIG. 10 shows a non-limiting embodiment of an absorptive device 72 has a body facing side 74 which is positioned against the user's body. The absorptive device 72 is made of, at least, a backsheet 76, an absorbent core 78, and a topsheet 80. The backsheet 76 is opposite the body facing side 74. The absorbent core 78 is between the backsheet 76 and the body facing side 74. The topsheet 80 is between the absorbent core 78 and the body facing side 74. It is understood that additional layers may be present between the absorbent core and the topsheet and backsheet, and that additional layers and other materials may be present on the side opposite the absorbent core from either the topsheet or the backsheet.

Method

Figure 11:
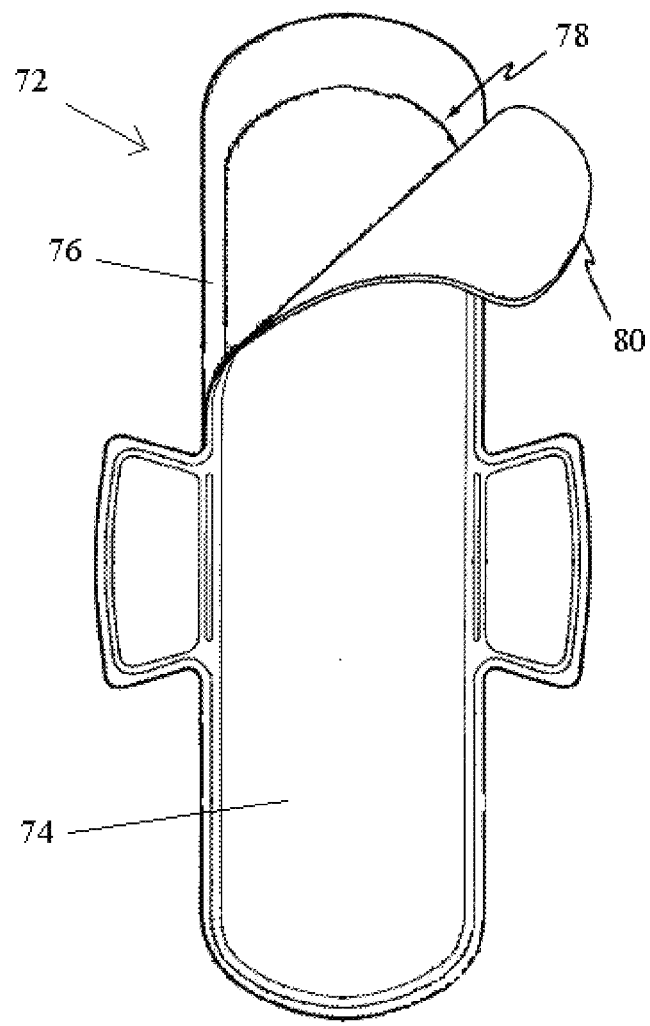
FIG. 11 is a plane view of an embodiment of an absorptive device.

FIG. 11 depicts an example embodiment of a process or method for forming an apertured film with light trap micro-pits. As shown in FIG. 11, an extrusion slot die 82 introduces a molten polymer web 84 that is delivered to a forming screen assembly 86 and a roller assembly 88 at an impingement point 90. For vacuum apertured formed films the most common polymer in use is primarily of, for example, polyolefin polymers such as polyethylene and such as those described in Thomas U.S. Pat. No. 4,456,570. For these general blend types the molten phase is maintained at a temperature above the temperature of melting (Tm) of the polymer web 82 such as a temperature of about 275° F. to 600° F. (135° C.-315° C.).

The forming screen assembly 86 includes a forming screen 58 and a stationary manifold 92 around which the forming screen 58 rotates. The screen apertures 68 enable air to pass through the forming screen 58 such that forming screen 58, and the screen apertures 68, form apertures (42, 48, 54) in the polymer web 84.

As shown in FIG. 11, the stationary manifold 92, around which the forming screen 58 rotates, includes a stationary vacuum slot 94 with a leading edge 96 and a trailing edge 98. The vacuum slot 94 defined between the leading edge 96 and the trailing edge 98 includes a zone of a pressure differential such that the vacuum slot 94 forms apertures (42, 48, 54) (e.g. via the pressure differential) in the polymer web 82 when the polymer web 82 thereon is passing beyond the leading edge 96, over the vacuum slot 94 and toward trailing edge 98. The pressure differential (negative pressure) provides for the forming of the apertures and lands and quenches the polymer web 84 and passes out of vacuum slot 94.

Additionally, the roller 100 has particular roller surface structure 102 that should have dimensions such as a particular length, diameter, and the like to insure that the light trap micro-pits 28 form uniformly in a random pattern onto the surface of polymer web 84 and subsequently the apertures are then formed through the polymer web 84. For example, if the roller 100 has a diameter that is too large (e.g. 6 inches [152 mm] or more, for example), the roller 10 can block air flow into the vacuum slot 94 such that the apertures can not properly form in the polymer web 84. As such, the roller 100 can have a diameter of about 2.0 inches (50.8 mm) to 5.5 inches (140 mm). The position of the roller 100 is dependent upon the desired thermal balance. Various possibilities exist for the manipulation of the parameters required in order to achieve a thermal balance. For example, to achieve the desired input heat of the melt stream at a desired impingement point 90, it is possible to vary both the length of the melt stream and the temperature of the molten polymer web 84 as it exits the lip of extrusion die slot 82. Thus, the key element of entering the impingement point 90 in the molten state (that is above the temperature of melting) will largely depend on the melting temperature of the specific polymer, or blends of polymers, in use at the time.

Without being limited by a theory, it is believed that the roller surface structure 102 provides a desired surface to form the light trap micro-pits 28 in the first side 12 of the polymer web 84. The roller surface 102 contacts the polymer web 84 at the impingement point 90, forming the light trap micro-pits 28 in the first side 12 of the polymer web 84 replicating the roller surface structure 102 into polymer web 84 while passing over the leading edge 96 of the vacuum slot 94. Continuing on over vacuum slot 94, the polymer web 84 forms apertures (42, 48, 54) creating an apertured formed film 10. In one embodiment, if the forming screen 58 has a non-uniform surface, such as a series of random humps and valleys, then the second surface 18 of the polymer web 84 conforms to the forming screen 58 and the non-uniform surface is replicated through the film thickness 14 of the polymer web 84 such that an apertured formed film comprises a non-uniform surface, such as a series of random humps and valleys with light trap micro-pits applied thereon.

Roller Surfaces

The light trap micro-pits 28 are formed from the interaction of the roller surface structure 102 and the polymer web 84 while the polymer web 84 is on the forming screen 58. In some embodiments, the selection of the roller surface structure 102 may require a particular forming screen 58 selection in order to achieve the desired light trap micro-pit formation.

One embodiment for the roller surface structure 102 may comprise a roughened surface of a cured photosensitive material of a pattern coded as C-HE80 available from Bright View Technologies. The surface of the C-HE80 roller surface structure 102 impinges on the polymer web 84 to result in the formation of the light trap micro-pits. The roller 100 construction to support a C-HE80 roller surface structure 102 is a metal cylinder with a thin rubber layer with the C-HE80 layer applied on the outside diameter of the roller 100.

The selection of the C-HE80 roller surface structure 102 is used in conjunction with a rubber screen. Suitable rubber screens may similar to those discussed in US 2010-0151191 A1. The rubber is from any class of Ebonite® Rubber or synthetic rubber such as HNBR having a hardness of about 75 Shore D. If desired, the forming screen 58 may be ground roughly on the primary plane to give a non-uniform surface, such as a series of random humps and valleys to the forming screen 58 in the primary plane 60.

One embodiment for the roller surface structure 102 may comprise a roughened surface of a metal cylinder whereupon the roughened outer layer is Galvanic Plated Nickel (GV). The surface of the GV roller surface structure 102 impinges on the polymer web 84 to result in the formation of the light trap micro-pits 28. The roller 100 construction to support a GV roller surface structure 102 is a metal cylinder with the GV layer applied on the outside diameter of the roller 100.

The selection of the GV roller surface structure 102 is used in conjunction with a metal screen or a rubber screen like those of discussed in US 2010-0151191 A1 which is laser cut to form a pattern of apertures between the lands. The rubber is from any class of EBONITE® Rubber or synthetic rubber such as hydrogenated nitrile butadiene rubber (HNBR) having a hardness of about 75 Shore D. If desired, a metal screen may be modified on the primary plane 60 to give a non-uniform surface, such as a series of random humps and valley. Metal screens may be modified by Plasma Coated (PC) layer which enhances the effect of lower gloss, providing the light diffusing pattern of humps and valleys on the primary plane of the screen lands 66. If desired, a rubber screen may be ground roughly on the primary plane to give a light diffusing pattern, such as a series of random humps and valleys to the rubber screen in the primary plane 60.

One embodiment for the roller surface structure 102 may comprise fiber ends formed from pressed felt materials cut into donut felts with fiber ends such as wool felts with fiber ends, and the like. The fiber ends are orientated to be perpendicular to the roller 100 and the fiber ends form the roller surface structure 102.

Figure 12:
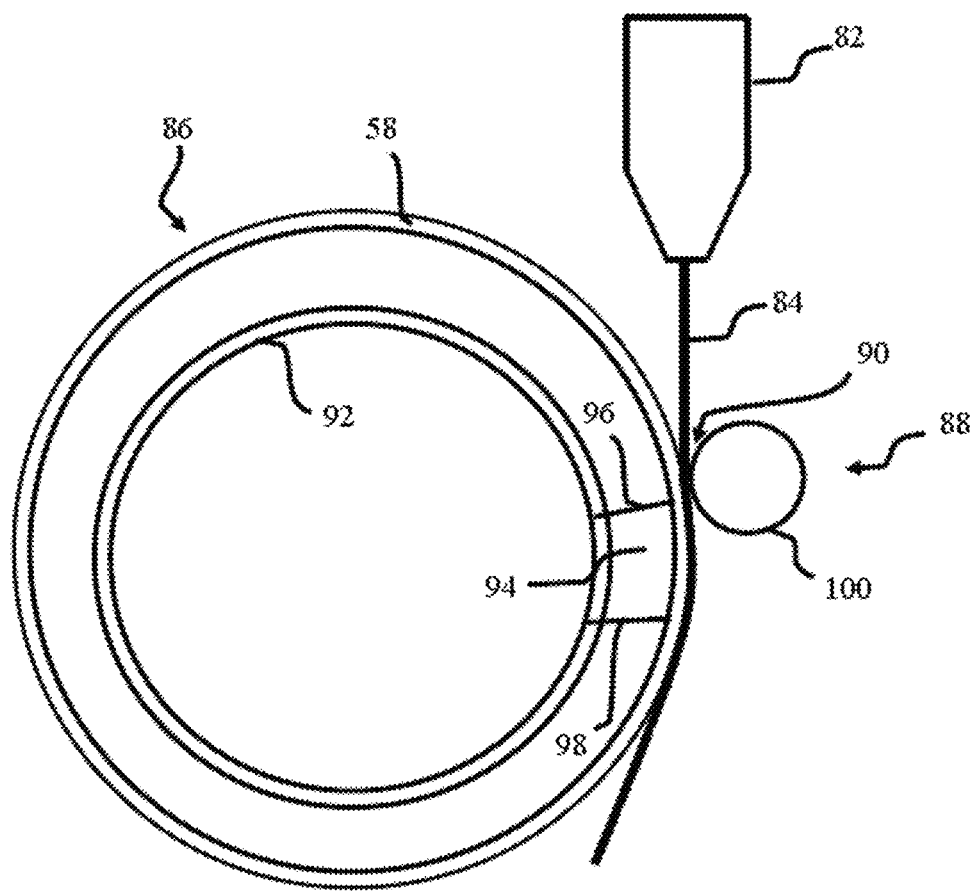
FIG. 12 depicts an example embodiment of a process or method for forming an apertured film with light trap micro-pits.
Figure 13:
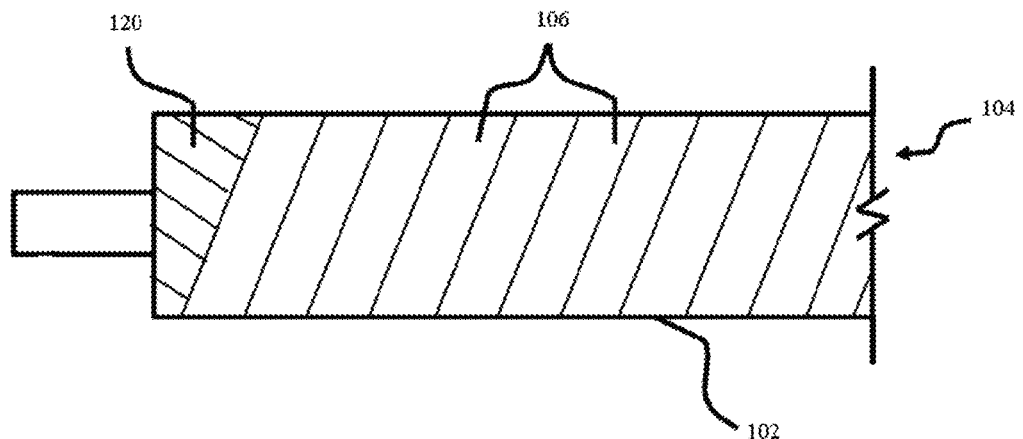
FIG. 13 a front view of a roller and a roller surface.
Figure 14:
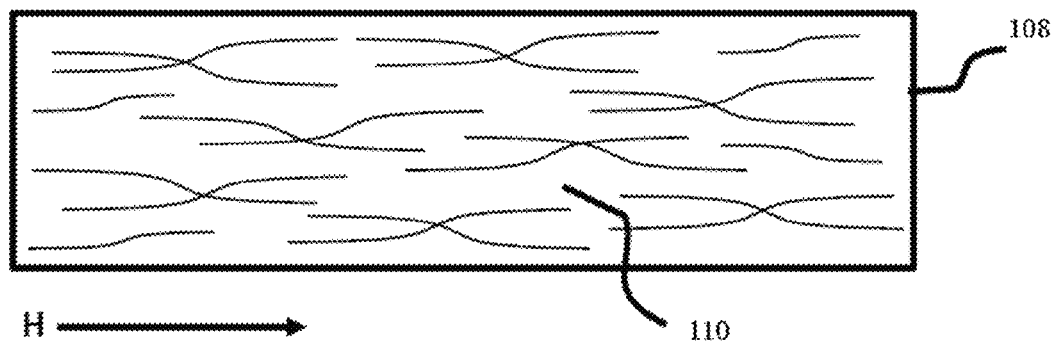
FIG. 14 a cross sectional view of the material for a roller surface.
Figure 15:
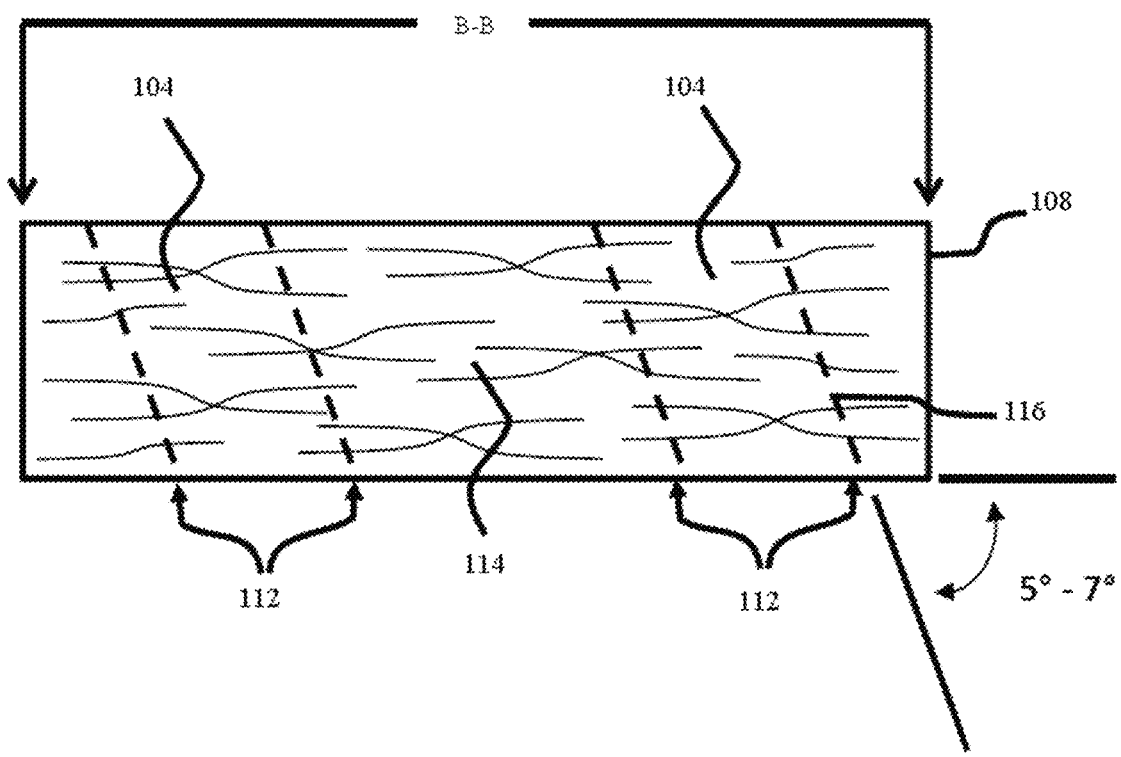
FIG. 15 a cross sectional view of the material for a roller surface showing a bias cut.
Figure 16:
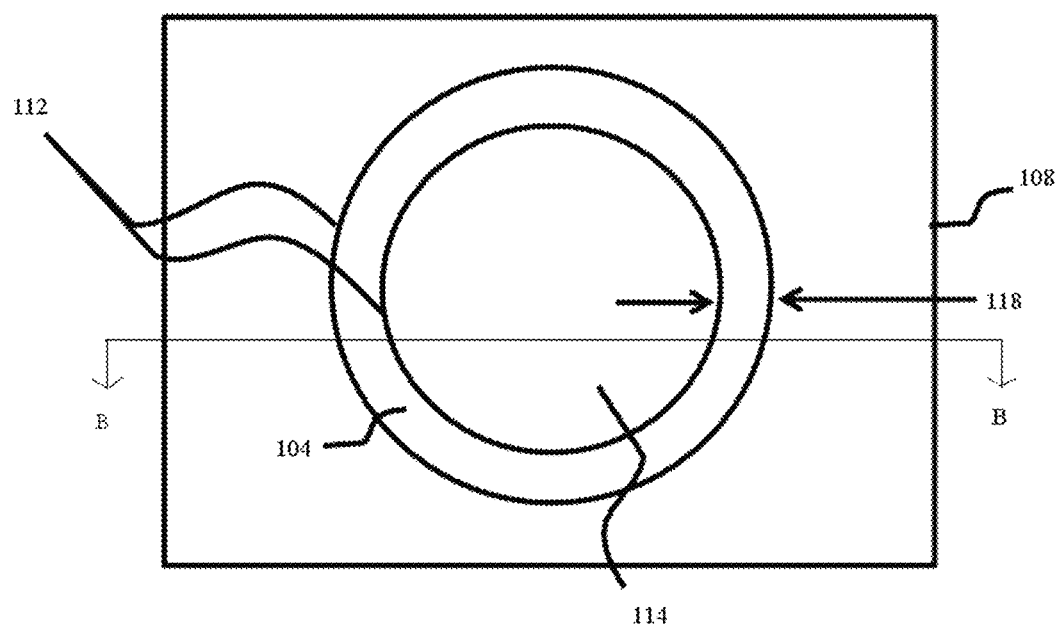
FIG. 16 a plane view of the material of FIG. 15.

FIG. 12 depicts an example embodiment of a front view of bias donut roller 104 having a roller surface structure 102 comprising one or more bias cut pressed felt sections 106. FIG. 13 depicts an example embodiment of a material 108 that may be used in a bias donut roller 104 in FIG. 12. In an example embodiment, the material 108 may be a pressed felt laid in a horizontal direction H. The material 108 may include one or more fibers 110 such as wool fibers that may also be oriented along the horizontal direction H. FIG. 14 depicts an example embodiment of a cross-section of a segment of the material 108 of along B-B as shown in FIG. 15. As shown in FIG. 14, the cross-section of a segment of the material 108 may have one or more cut lines 112. The cut lines 112 may be out of or from a felt donut by, for example, severing horizontal fibers at one or more severed horizontal fiber points. In an embodiment, the cut lines 112 may be on a biased angle from at least about 5° to about 7°. When placing the donuts on a biased angle from at least about 5° to about 7°, there is no continuous machine direction line present as the donuts may rotate and, as such, no visible flaw may be provided in the film surface.

The material 108 may include a center cut portion 114 and an outer ring cut 116 formed by the cut lines 112. In an embodiment, the center cut portion 114 may become the donut-hole and may be a throw-away piece while the outer ring cut 116 may be the donut or donut felt that may be used for the roller surface structure 102 or cover of the roller. FIG. 15 depicts an example embodiment of a plane or end view of the section 106 of FIG. 12 with the cut lines 112, thrown away center cut portion 114, and the outer ring cut 116. As shown in FIG. 15, the donut ring felt section 106 may have a wall thickness 118 of at least about 0.50 inches (12.7 mm) to about 0.75 inches (19 mm).

More than one section 106 may be stacked and pressed together to form a bias donut roller 104 having a roller surface structure 102. The bias donut roller 104 may further include an end cap 120. In an example embodiment, the end cap 120 wherein one side or portion of the end cap 120 may be non-square such that the end cap 120 may have a corresponding bias angle section 122. Additionally, the roller surface structure 102 may be ground to a consistent TIR (True Indicated Runout).

Additionally, as shown in FIG. 7, the roller 100 is positioned at the leading edge 96 in one embodiment such that the roller 100 is in virtually simultaneous contact with the polymer web 84 when delivered to forming screen 58 at the impingement point 90.

As shown in FIG. 11, after forming light trap micro-pits 28 at the impingement point 90, the polymer web 84 with a random pattern of light trap micro-pits 28 formed thereon is then passed beyond the leading edge 96 over the vacuum slot 94. As described above, in one embodiment, the forming screen 58 further has one or more screen apertures 68 of a certain shape and in a certain pattern, for example, surrounded by and adjacent to the screen lands 66. When passing the polymer web 84 beyond the leading edge 96 and past the impingement point 90 of the roller 100, it continues over the vacuum slot 94.

The molten polymer web 84 suspended over the screen apertures 68 in the forming screen 50 is pulled into the screen apertures 68 (not shown) by the pressure differential created in the vacuum slot 94 such that apertures (42, 48, 54) are formed in those corresponding regions of the polymer web 84. Conductive cooling of the air passing through the newly formed apertures (42, 48, 54) then removes sufficient heat from the molten polymer web 58 to cause it to change from the molten phase to the solid phase. When in the solid phase, the polymer web 58 does not loose its newly formed shapes or structures for neither the micro scale light trap micro-pits 28 on the lands with humps and valleys, nor the macro-aperture scale.

The forming screen 58 rotates or moves such that the apertured film with light trap micro-pits 10 passes beyond the trailing edge 98 of the vacuum slot 94. After passing over the trailing edge 98 of the vacuum slot 94, the apertured film with light trap micro-pits 10 is peeled off of the forming screen 58 by a peel roller (not shown).

According to embodiments, the apertured formed film with a plurality of light trap micro-pits can further be provided to or passed to additional components or equipment such that the apertured formed film is cut to desired width dimensions and wound in rolls for conversion as a component, most probably a topsheet, of any variety of absorptive devices and functions thereto.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An apertured film comprising an apertured film surface area comprising a pattern of apertures and lands surrounding the apertures, the lands comprising a land area; the land area comprising a plurality of light trap micro-pits randomly positioned on the land area with uniform density across the land area and a total reflective area, each of the light trap micro-pits comprising an opening with a sidewall descending from the opening to a bottom; wherein each of the openings of the light trap micro-pits comprises an irregular perimeter with an average diameter and a depth greater than half the average diameter of the micro-pit divided by tan 37.5, wherein the apertured film surface area comprises a 75° gloss in the machine direction of the apertured film of less than 4.0.

2. The apertured film of claim 1, wherein the light trap micro-pit average diameter is no more than about 250 µm and no less than about 25 µm.

3. The apertured film of claim 1, wherein the total reflective area is less than the land area.

4. The apertured film of claim 1, wherein the 75° gloss in the machine direction of the apertured film is less than 3.5.

5. The apertured film of claim 1, wherein the light trap micro-pits have an edge-to-edge spacing of less than 155 µm.

6. The apertured film of claim 1, wherein the pattern of apertures is selected from a 50/7 pattern, 35/7 pattern, 35/14 pattern and combinations thereof.

7. The apertured film of claim 1, wherein the land area further comprises a series of random humps and valleys.

8. The apertured film of claim 1, wherein the pattern of apertures comprises nested pentagons with a substantially uniform land between the apertures defining a land width of about 178 microns yielding a land area of about 40% of the total surface area.

* * * * *